(12) United States Patent
Ingraham et al.

(10) Patent No.: US 6,890,925 B2
(45) Date of Patent: May 10, 2005

(54) METHODS OF USING SOLUBLE EPOXIDE HYDROLASE INHIBITORS

(75) Inventors: Richard H. Ingraham, New Fairfield, CT (US); John R. Proudfoot, Newtown, CT (US)

(73) Assignee: Boehringer Ingelheim Pharmaceuticals, Inc., Ridgebury, CT (US)

( * ) Notice: Subject to any disclaimer, the term of this patent is extended or adjusted under 35 U.S.C. 154(b) by 0 days.

(21) Appl. No.: 10/670,668

(22) Filed: Sep. 25, 2003

(65) Prior Publication Data

US 2004/0092567 A1 May 13, 2004

Related U.S. Application Data

(63) Continuation of application No. 10/172,457, filed on Jun. 14, 2002.
(60) Provisional application No. 60/302,066, filed on Jun. 29, 2001.

(51) Int. Cl.[7] ............... A61K 31/5375; C07D 413/412; C07D 413/414
(52) U.S. Cl. ................. 514/235.8; 544/124; 546/268.1; 546/275.7; 548/356.1; 548/364.1; 514/231.2; 514/406
(58) Field of Search ...................... 544/124; 548/356.1, 548/364.1; 514/235.8, 231.2, 406; 546/268.1, 275.7

(56) References Cited

U.S. PATENT DOCUMENTS 6,348,480 B1    2/2002  Kubota et al.

6,506,747 B1    1/2003  Betageri et al.

FOREIGN PATENT DOCUMENTS

WO      WO 99/62885    * 12/1999

OTHER PUBLICATIONS

James M. Trevillyan, et al; Potent Inhibition of NFAT Activation and T Cell Cytokine Production by Novel Low Molecular Weight Pyrazole Compounds, Journal of Biological Chemistry, vol. 276, No. 51 pp. 48118–48126, 2001.

Christof Zitt, et al; Potent Inhibition of Ca2+ Release–activated Ca2+ Channels and T–lymphocyte Activation by the Pyrazole Derivative BTP2 , Journal of Biological Chemistry, vol. 279, No. 13, Issue of Mar. 26, pp12427–12437, 2004.

Jun Ishikawa, et al; A Pyrazole Derivative, YM–58483, Potently Inhibits Store–Operated Sustained Ca2+ Influx and IL–2 Production in T Lymphocytes, The Journal of Immunology pp. 4441–4449.

Steven Djuric, et al; 3–5 Bis(trifluoromethyl)pyrazoles: A Novel Class of NFAT Transcription Factor Regulator, Journal of Med. Chem, 2000, 43, 2975–2981.

Yung–Wu Chen, et al; TH1 and TH2 cytokine inhibition by 3–5 Bis(trifluoromethyl) pyrazoles, a novel class of immunomodulators, Cellular Immunology 220 (2002) 134–142.

* cited by examiner

Primary Examiner—Golam M M Shameem
(74) Attorney, Agent, or Firm—Michael P. Morris; Anthony P. Bottino; Philip I. Datlow

(57) ABSTRACT

Disclosed are methods of using soluble epoxide hydrolase (sEH) inhibitors of the formulas I and Ia for diseases related to cardiovascular disease.

7 Claims, No Drawings

METHODS OF USING SOLUBLE EPOXIDE HYDROLASE INHIBITORS

RELATED APPLICATION DATA

This application is a continuation of U.S. application Ser. No. 10/172,457, filed Jun. 14, 2002, which claims benefit to U.S. provisional application No. 60/302,066 filed Jun. 29, 2001.

FIELD OF THE INVENTION

This invention is directed to methods of using soluble epoxide hydrolase (sEH) inhibitors for diseases related to cardiovascular disease.

BACKGROUND OF THE INVENTION

Epoxide hydrolases are a group of enzymes ubiquitous in nature, detected in species ranging from plants to mammals. These enzymes are functionally related in that they all catalyze the addition of water to an epoxide, resulting in a diol. Epoxide hydrolases are important metabolizing enzymes in living systems. Epoxides are reactive species and once formed are capable of undergoing nucleophilic addition. Epoxides are frequently found as intermediates in the metabolic pathway of xenobiotics. Thus in the process of metabolism of xenobiotics, reactive species are formed which are capable of undergoing addition to biological nucleophiles. Epoxide hydrolases are therefore important enzymes for the detoxification of epoxides by conversion to their corresponding, non-reactive diols.

In mammals, several types of epoxide hydrolases have been characterized including soluble epoxide hydrolase (sEH), also referred to as cytosolic epoxide hydrolase, cholesterol epoxide hydrolase, $LTA_4$ hydrolase, hepoxilin hydrolase, and microsomal epoxide hydrolase (Fretland and Omiecinski, Chemico-Biological Interactions, 129: 41–59 (2000)). Epoxide hydrolases have been found in all tissues examined in vertebrates including heart, kidney and liver (Vogel, et al., Eur J. Biochemistry, 126: 425–431 (1982); Schladt et al., Biochem. Pharmacol., 35: 3309–3316 (1986)). Epoxide hydrolases have also been detected in human blood components including lymphocytes (e.g. T-lymphocytes), monocytes, erythrocytes, platelets and plasma. In the blood, most of the sEH detected was present in lymphocytes (Seidegard et al., Cancer Research, 44: 3654–3660(1984)).

The epoxide hydrolases differ in their specificity towards epoxide substrates. For example, sEH is selective for aliphatic epoxides such as epoxide fatty acids while microsomal epoxide hydrolase (mEH) is more selective for cyclic and arene oxides. The primary known physiological substrates of sEH are four regioisomeric cis epoxides of arachidonic acid known as epoxyeicosatrienoic acids or EETs. These are 5,6-, 8,9-, 11,12-, and 14,15-epoxyeicosatrienoic acid. Also known to be substrates are epoxides of linoleic acid known as leukotoxin or isoleukotoxin. Both the EETs and the leukotoxins are generated by members of the cytochrome P450 monooxygenase family (Capdevila, et al., J. Lipid Res., 41: 163–181 (2000)).

The various EETs appear to function as chemical mediators that may act in both autocrine and paracrine roles. EETs appear to be able to function as endothelial derived hyperpolarizing factor (EDHF) in various vascular beds due to their ability to cause hyperpolarization of the membranes of vascular smooth muscle cells with resultant vasodilation (Weintraub, et al., Circ. Res., 81: 258–267 (1997)). EDHF is synthesized from arachidonic acid by various cytochrome P450 enzymes in endothelial cells proximal to vascular smooth muscle (Quilley, et al., Brit. Pharm., 54: 1059 (1997)); Quilley and McGiff, TIPS, 21: 121–124 (2000)); Fleming and Busse, Nephrol. Dial. Transplant, 13: 2721–2723 (1998)). In the vascular smooth muscle cells EETs provoke signaling pathways which lead to activation of $BK_{Ca2+}$ channels (big $Ca^{2+}$ activated potassium channels) and inhibition of L-type $Ca^{2+}$ channels. This results in hyperpolarization of membrane potential, inhibition of $Ca^{2+}$ influx and relaxation (Li et al., Circ. Res., 85: 349–356 (1999)). Endothelium dependent vasodilation has been shown to be impaired in different forms of experimental hypertension as well as in human hypertension (Lind, et al., Blood Pressure, 9: 4–15 (2000)). Impaired endothelium dependent vasorelaxation is also a characteristic feature of the syndrome known as endothelial dysfunction (Goligorsky, et. al., Hypertension, 37[part 2 ]:744–748 ( 2001). Endothelial dysfunction plays a significant role in a large number of pathological conditions including type 1 and type 2 diabetes, insulin resistance syndrome, hypertension, atherosclerosis, coronary artery disease, angina, ischemia, ischemic stroke, Raynaud's disease and renal disease. Hence, it is likely that enhancement of EETs concentration would have a beneficial therapeutic effect in patients where endothelial dysfunction plays a causative role. Other effects of EETs that may influence hypertension involve effects on kidney function. Levels of various EETs and their hydrolysis products, the DHETs, increase significantly both in the kidneys of spontaneously hypertensive rats (SHR) (Yu, et al., Circ. Res. 87: 992–998 (2000)) and in women suffering from pregnancy induced hypertension (Catella, et al., Proc. Natl. Acad. Sci. U.S.A., 87: 5893–5897 (1990)). In the spontaneously hypertensive rat model, both cytochrome P450 and sEH activities were found to increase (Yu et al., Molecular Pharmacology, 2000, 57, 1011–1020). Addition of a known sEH inhibitor was shown to decrease the blood pressure to normal levels. Finally, male soluble epoxide hydrolase null mice exhibited a phenotype characterized by lower blood pressure than their wild-type counterparts (Sinal, et al., J.Biol.Chem., 275: 40504–40510 (2000)).

EETs, especially 11,12- EET, also have been shown to exhibit anti-inflammatory properties (Node, et al., Science, 285: 1276–1279 (1999); Campbell, TIPS, 21: 125–127 (2000); Zeldin and Liao, TIPS, 21: 127–128 (2000)). Node, et al. have demonstrated 11,12-EET decreases expression of cytokine induced endothelial cell adhesion molecules, especially VCAM-1. They further showed that EETs prevent leukocyte adhesion to the vascular wall and that the mechanism responsible involves inhibition of NF-κB and IκB kinase. Vascular inflammation plays a role in endothelial dysfunction (Kessler, et al., Circulation, 99: 1878–1884 (1999)). Hence, the ability of EETs to inhibit the NF-κB pathway should also help ameliorate this condition.

In addition to the physiological effect of some substrates of sEH (EETs, mentioned above), some diols, i.e. DHETs, produced by sEH may have potent biological effects. For example, sEH metabolism of epoxides produced from linoleic acid (leukotoxin and isoleukotoxin) produces leukotoxin and isoleukotoxin diols (Greene, et al., Arch. Biochem. Biophys. 376(2): 420–432 (2000)). These diols were shown to be toxic to cultured rat alveolar epithelial cells, increasing intracellular calcium levels, increasing intercellular junction permeability and promoting loss of epithelial integrity (Moghaddam et al., Nature Medicine, 3: 562–566 (1997)). Therefore these diols could contribute to the etiology of diseases such as adult respiratory distress syndrome where lung leukotoxin levels have been shown to be elevated (Ishizaki, et al., Pulm. Pharm.& Therap., 12: 145–155 (1999)). Hammock, et al. have disclosed the treatment of inflammatory diseases, in particular adult respiratory distress syndrome and other acute inflammatory conditions mediated by lipid metabolites, by the administration of inhibitors of epoxide hydrolase (WO 98/06261; U.S. Pat. No. 5,955,496).

A number of classes of sEH inhibitors have been identified. Among these are chalcone oxide derivatives (Miyamoto, et al. Arch. Biochem. Biophys., 254: 203–213 (1987)) and various trans-3-phenylglycidols (Dietze, et al., Biochem. Pharm. 42: 1163–1175 (1991); Dietze, et al., Comp.Biochem. Physiol. B, 104: 309–314 (1993)).

More recently, Hammock et al. have disclosed certain biologically stable inhibitors of sEH for the treatment of inflammatory diseases, for use in affinity separations of epoxide hydrolases and in agricultural applications (U.S. Pat. No. 6,150,415). The Hammock '415 patent also generally describes that the disclosed pharmacophores can be used to deliver a reactive functionality to the catalytic site, e.g., alkylating agents or Michael acceptors, and that these reactive functionalities can be used to deliver fluorescent or affinity labels to the enzyme active site for enzyme detection (col. 4, line 66 to col. 5, line 5). Certain urea and carbamate inhibitors of sEH have also been described in the literature (Morisseau et al., Proc. Natl. Acad. Sci., 96: 8849–8854 (1999); Argiriadi et al., J. Biol. Chem., 275 (20) 15265–15270 (2000); Nakagawa et al. Bioorg. Med. Chem., 8: 2663–2673 (2000)).

WO 99/62885 (A1) discloses 1-(4-aminophenyl) pyrazoles having anti-inflammatory activity resulting from their ability to inhibit IL-2 production in T-lymphocytes, it does not however, disclose or suggest compounds therein being effective inhibitors of sEH. WO 00/23060 discloses a method of treating immunological disorders mediated by T-lymphocytes by administration of an inhibitor of sEH. Several 1-(4-aminophenyl)pyrazoles are given as examples of inhibitors of sEH.

As outlined in the discussion above, inhibitors of sEH are useful therefore, in the treatment of cardiovascular diseases such as endothelial dysfunction either by preventing the degradation of sEH substrates that have beneficial effects or by preventing the formation of metabolites that have adverse effects. Further investigation by the present inventors has shown that the inhibition of IL-2 production and inhibition of sEH are separable activities with divergent structure-activity relationships. New embodiments of 1-(4-aminophenyl)pyrazoles, potent and selective for inhibition of sEH are disclosed herein.

All references cited above and throughout this application are incorporated herein by reference in their entirety.

SUMMARY OF THE INVENTION

It is therefore an object of the invention to provide a method of treating a cardiovascular disease; said method comprising administering to a patient in need thereof a therapeutically effective amount of a compound of Formula I:

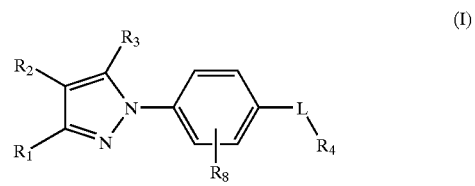

wherein:
$R_1$ and $R_3$ are the same or different and each is $CF_3$, halogen, CN, $C_{1-8}$ alkyl or branched alkyl, $C_{2-8}$ alkenyl or $C_{3-8}$ branched alkenyl, $C_{2-8}$ alkynyl or $C_{3-8}$ branched alkynyl, $C_{3-8}$ cycloalkyl optionally substituted with OH, CN or methoxy, $C_{1-8}$ alkyloxy, $C_{1-4}$ alkyloxy$C_{1-4}$ alkyl, $C_{1-8}$ alkylthio, $C_{1-4}$ alkylthio$C_{1-4}$alkyl, $C_{1-8}$ dialkylamino, $C_{1-4}$ dialkylaminoalkyl, $CO_2R_5$ where $R_5$ is $C_{1-4}$ alkyl or $C_{2-4}$ alkenyl optionally substituted with carbocyclyl or heterocyclyl, aryl or $R_1$ and $R_3$ are heterocyclyl connected to the pyrazole in any position that makes a stable bond optionally substituted with halogen, $C_{1-4}$ alkyl, $C_{2-4}$ alkenyl, CN, $(CH_3)_2N$, $CO_2CH_3$, alkyloxy, aryl, heterocyclyl or $R_5$;
$R_2$ is H, halogen or methyl;
L is —NHC(O)—, —NHC(O)O—, —NHC(O)C(O)—, —NHC(S)—, —NH—, —NHC(O)NH, NHC(S)NH, NHCH$_2$, —NHCH($R_6$)—, where $R_6$ is H, CN or $C_{1-3}$ alkyl,
$R_4$ is $C_{1-8}$ alkyl, $C_{1-8}$ alkyloxy, $C_{1-8}$ alkylthio, $C_{1-8}$ alkylamino, $C_{1-4}$ alkyloxyalkyl, $C_{1-4}$ alkylthioalkyl, $C_{1-4}$alkylaminoalkyl, $C_{1-4}$dialkylaminoalkyl, carbocyclyl or heterocyclyl each optionally substituted with one or more halogen, —CN, —NO$_2$, SO$_2$NH$_2$ alkylthio, alkylsulfinyl, alkylsulfonyl or $R_7$ where $R_7$ is phenyl, heterocyclyl, $C_{3-6}$cycloalkyl, $C_{1-6}$ alkyl, $C_{2-6}$ alkenyl, $C_{1-6}$ alkyloxyalkyl, $C_{1-4}$ alkyloxy, $C_{1-5}$ alkylamino, $C_{1-6}$ alkylthioalkyl, $C_{1-6}$ alkylsulfinylalkyl or $C_{1-6}$ alkylsulfonylalkyl, each $R_7$ in turn is optionally substituted with halogen, OH, alkyloxy, CN, COO-lower alkyl, —CONH-lower alkyl, —CON(lower alkyl)$_2$, dialkylamino, phenyl or heterocyclcyl;
$R_8$ is H or NH$_2$;
or the pharmaceutically acceptable derivatives thereof;
with the proviso that when $R_3$ is alkyl or $CF_3$ and $R_4$ is pyridyl, then the pyridyl is substituted except that the substituents on the pyridyl cannot be halogen; and with the proviso that the following compounds are excluded: N-[4-(5-ethyl-3-pyridin-3-yl-pyrazol-1-yl)-phenl]-nicotinamide; N-[4-(5-Ethyl-3-pyridin-3-yl-pyrazol-1-yl) phenyl]-1-methylindole-2-carboxamide; 4-(3-Cyanopropoxy)-N-[4-(5-cyano-3-pyridin-3-yl-pyrazol-1-yl)phenyl]benzamide; and N-[4-(5-cyano-3-pyridin-3-yl-pyrazol- 1yl)phenyl]-4-(3-[1,3]dioxolan-2-yl-propoxy) benzamide.

DETAILED DESCRIPTION OF THE INVENTION

Preferred embodiments of the invention include:
The method as described in the broadest embodiment above and wherein:
in formula (I):
$R_1$ is $C_{1-8}$ alkyl or branched alkyl, $C_{3-8}$ alkenyl or branched alkenyl, $C_{3-8}$ alkynyl or branched alkynyl, $C_{3-8}$ cycloalkyl, $C_{1-3}$ alkyloxy$C_{1-3}$ alkyl, $C_{1-5}$ alkyloxy, $C_{1-3}$ alkylthio$C_{1-3}$ alkyl, $C_{1-5}$ alkylthio, $CF_3$, heterocyclyl selected from tetrahydrofuranyl, pyridyl, furanyl or thiazolyl or aryl optionally substituted with halogen, $C_{1-4}$ alkyl, CN, alkyloxy or $(CH_3)_2N$;

$R_2$ is H;

$R_3$ is halogen, methyl, ethyl, $CF_3$, CN, cyclopropyl, vinyl, $SCH_3$, methoxy, heterocyclyl selected from tetrahydrofuranyl, pyridyl, furanyl or thiazolyl or aryl optionally substituted with halogen, $C_{1-4}$ alkyl, CN, methoxy or $(CH_3)_2N$;

L is —NHC(O)—, —NH—, —NHCH$_2$—, —NHC(O)NH, and $R_4$ is $C_{1-6}$ alkyl, carbocyclyl or heterocyclyl selected from pyridyl, pyrimidinyl, pyrazinyl, pyridazinyl, morpholinyl, thiomorpholinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl, each optionally substituted with one or more halogen, —CN, alkylthio, alkylsulfinyl, alkylsulfonyl, —NO$_2$, SO$_2$NH$_2$ or $R_7$ where $R_7$ is $C_{1-6}$ alkyl, $C_{2-6}$ alkenyl, $C_{1-6}$ alkyloxyalkyl, $C_{1-4}$ alkyloxy, $C_{1-5}$ alkylamino, or $C_{1-6}$ alkylthioalkyl each optionally substituted with OH, CN, —COO-lower alkyl, —CONH-lower alkyl, —CON(lower alkyl)$_2$, dialkylamino, phenyl or heterocyclyl as hereinabove described in this paragraph; and $R_8$ is H or NH$_2$.

In another embodiment, there is provided the method as described in the embodiment immediately above and wherein:

in the formula (I)

$R_1$ is ethyl, isopropyl, n-propyl, t-butyl, cyclopentyl, $CF_3$, ethoxy, $CH_3OCH_2$—, 2- or 3-tetrahydrofuranyl 2-, 3-, or 4-pyridyl, 2-furanyl, or 2-thiazolyl;

$R_3$ is CN, $CF_3$, Cl, methyl, ethyl, $SCH_3$, cyclopropyl, vinyl or 2-furanyl;

L is —NHC(O)—, and $R_4$ is a phenyl or pyridyl each optionally substituted with one to three halogen, —CN, alkylthio, alkylsulfinyl, alkylsulfonyl or $R_7$ where $R_7$ is $C_{1-6}$ alkyl, $C_{2-6}$ alkenyl, $C_{1-6}$ alkyloxy$C_{1-6}$ alkyl, $C_{1-4}$ alkyloxy, $C_{1-5}$ alkylamino each optionally substituted with halogen, OH, CN, COO-lower alkyl, —CONH-lower alkyl, —CON(lower alkyl)$_2$, dialkylamino, phenyl, morpholinyl or pyridyl.

In yet another embodiment, there is provided the method as described in the embodiment immediately above and wherein:

in the formula (I)

$R_1$ is isopropyl, $CF_3$, 3-pyridyl or 4-pyridyl;

$R_2$ is H;

$R_3$ is CN, $CF_3$, Cl, methyl, $SCH_3$ or ethyl; and $R_4$ is a phenyl or pyridyl each optionally substituted with one to three groups selected from halogen, —CN, alkylthio, alkylsulfinyl, alkylsulfonyl or $R_7$ where $R_7$ is $C_{1-6}$ alkyl, $C_{1-4}$ alkyloxy, $C_{1-5}$ alkylamino each optionally substituted with OH, CN, COO-lower alkyl, —CONH-lower alkyl, —CON(lower alkyl)$_2$, dialkylamino, phenyl, morpholinyl or pyridyl.

In yet still another embodiment, there is provided a method of treating cardiovascular disease said method comprising administering to a patient in need thereof a therapeutically effective amount of a compound chosen from:

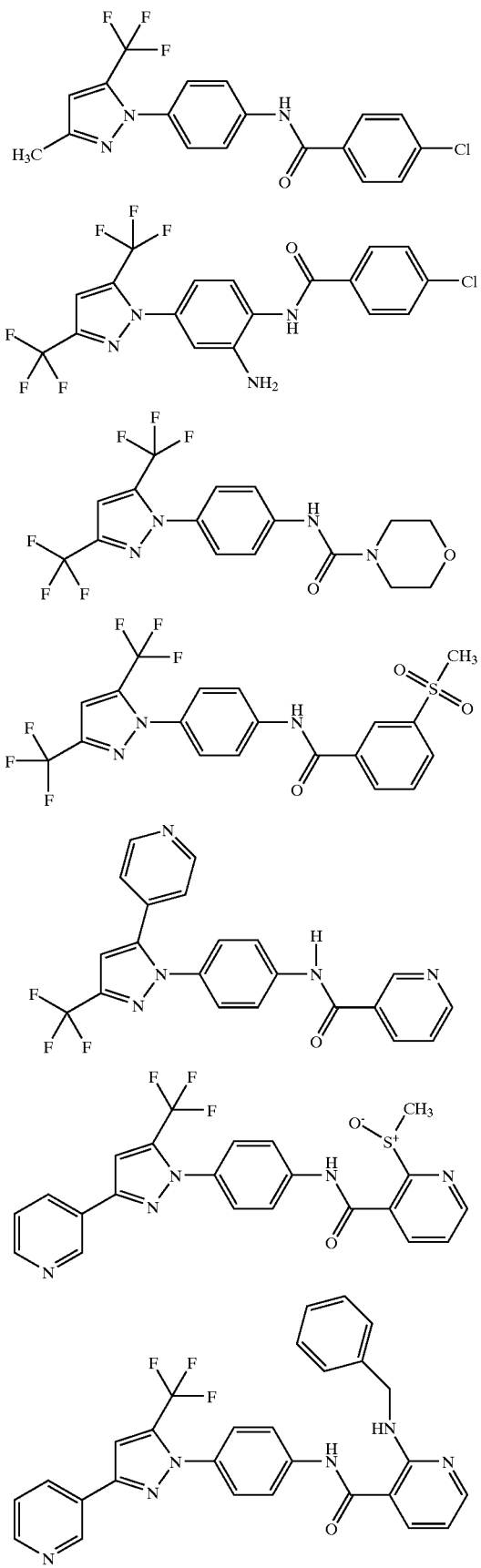

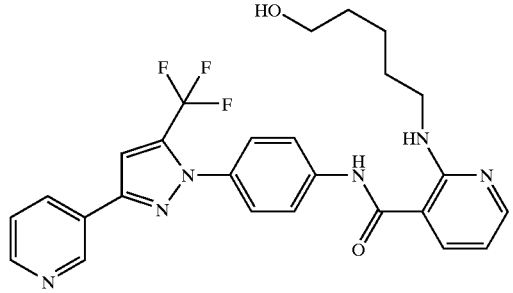
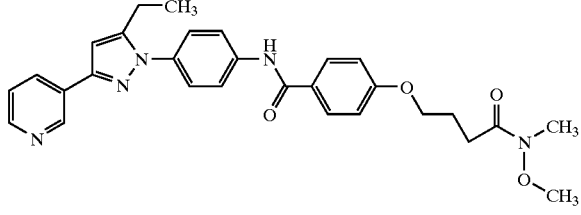
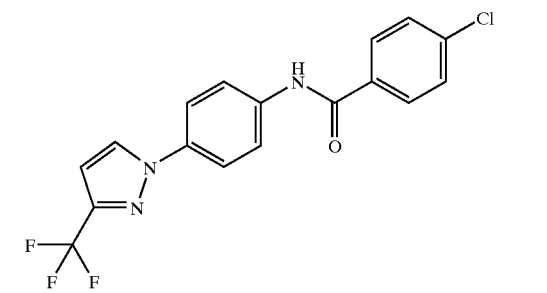
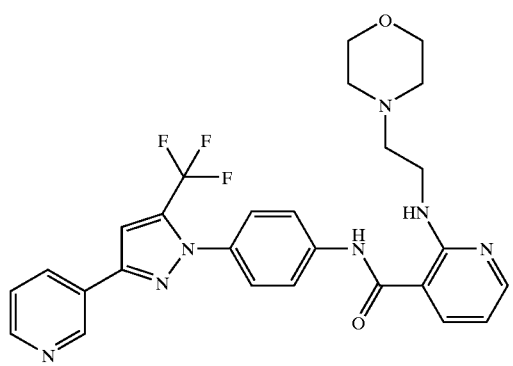
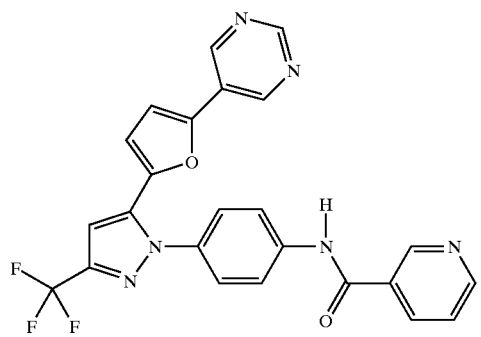
or the pharmaceutically acceptable derivatives thereof.
In yet still another embodiment, there is provided a method of treating cardiovascular disease said method comprising administering to a patient in need thereof a therapeutically effective amount of a compound chosen from:
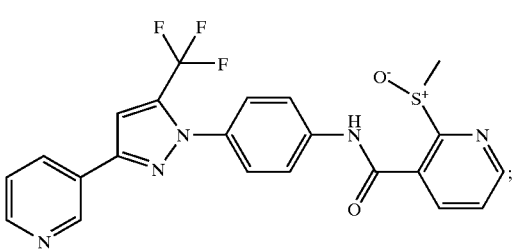
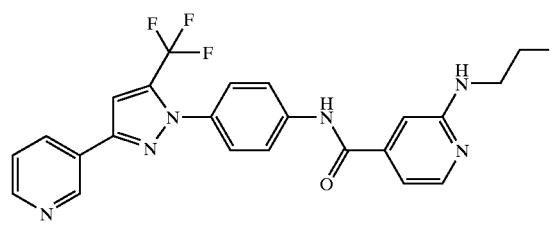
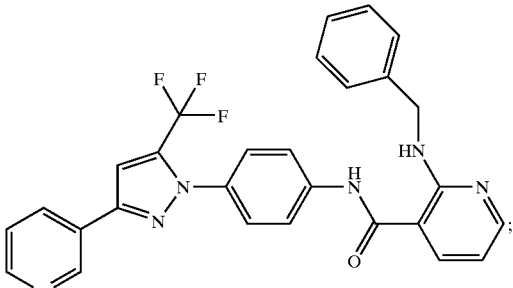
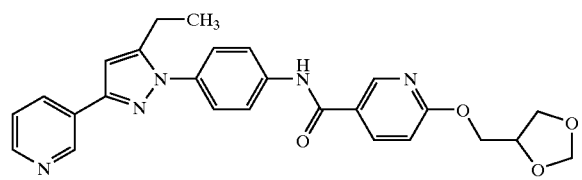
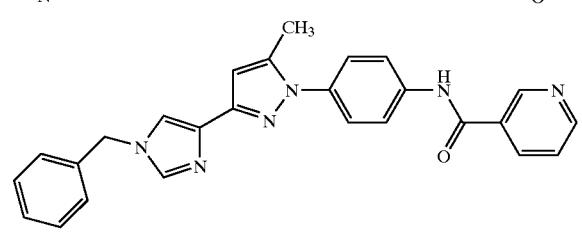
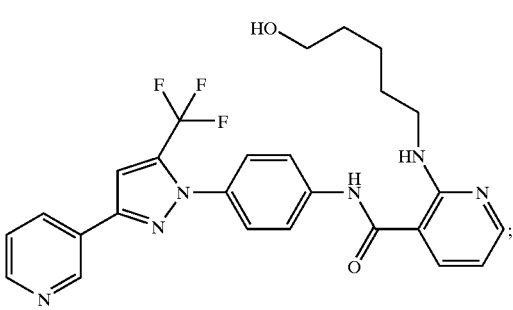

-continued

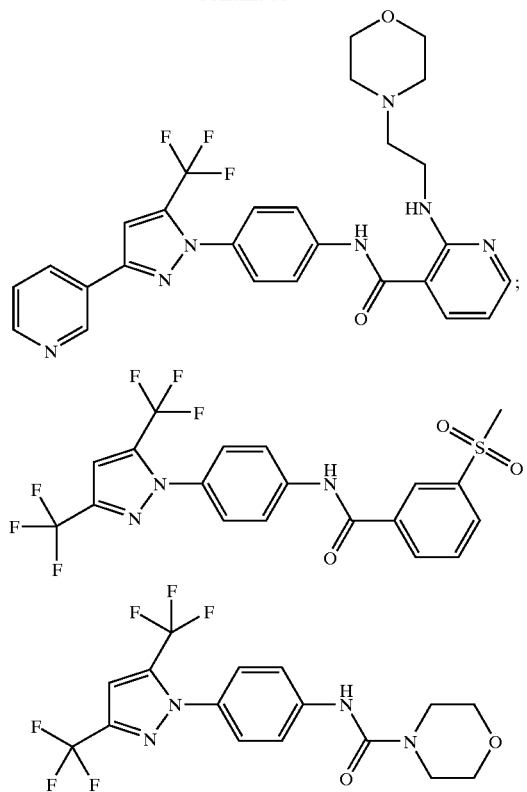

or the pharmaceutically acceptable derivatives thereof.

In yet another embodiment of the invention there are provided novel compounds of the formula (Ia)

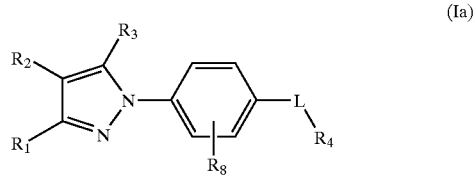

(Ia)

wherein:
$R_1$ and $R_3$ are the same or different and each is $CF_3$, halogen, CN, $C_{1-8}$ alkyl or branched alkyl, $C_{2-8}$ alkenyl or $C_{3-8}$ branched alkenyl, $C_{2-8}$ alkynyl or $C_{3-8}$ branched alkynyl, $C_{3-8}$ cycloalkyl optionally substituted with OH, CN or methoxy, $C_{1-8}$ alkyloxy, $C_{1-4}$alkyloxy$C_{1-4}$ alkyl, $C_{1-8}$ alkylthio, $C_{1-4}$ alkylthio$C_{1-4}$alkyl, $C_{1-8}$ dialkylamino, $C_{1-4}$ dialkylaminoalkyl, $CO_2R_5$ where $R_5$ is $C_{1-4}$ alkyl or $C_{2-4}$ alkenyl optionally substituted with carbocyclyl or heterocyclyl, aryl or $R_1$ and $R_3$ are heterocyclyl connected to the pyrazole in any position that makes a stable bond optionally substituted with halogen, $C_{1-4}$ alkyl, $C_{2-4}$ alkenyl, CN, $(CH_3)_2N$, $CO_2CH_3$, alkyloxy, aryl, heterocyclyl or $R_5$;
$R_2$ is H, halogen or methyl;
L is —NHC(O)—, —NHC(O)O—, —NHC(O)C(O)—, —NHC(S)—, —NH—, —NHC(O)NH, NHC(S)NH, NHCH$_2$, —NHCH($R_6$)—, where $R_6$ is H, CN or $C_{1-3}$ alkyl,
$R_4$ is $C_{1-8}$ alkyl, $C_{1-8}$ alkyloxy, $C_{1-8}$ alkylthio, $C_{1-8}$ alkylamino, $C_{1-4}$ alkyloxyalkyl, $C_{1-4}$ alkylthioalkyl, $C_{1-4}$alkylaminoalkyl, $C_{1-4}$dialkylaminoalkyl, carbocyclyl or heterocyclyl each optionally substituted with one or more halogen, —CN, —NO$_2$, SO$_2$NH$_2$ alkylthio, alkylsulfinyl, alkylsulfonyl or $R_7$ where $R_7$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-4}$ alkyloxy, $C_{1-5}$ alkylamino, $C_{1-6}$ alkylthioalkyl, $C_{1-6}$ alkylsulfmylalkyl or $C_{1-6}$ alkylsulfonylalkyl, each $R_7$ in turn is optionally substituted with halogen, OH, alkyloxy, CN, COO-lower alkyl, —CONH-lower alkyl, —CON(lower alkyl)$_2$, dialkylamino, phenyl or heterocylcyl;
$R_8$ is NH$_2$ or mono-or-diC1-5alkylamino;
or the pharmaceutically acceptable derivatives thereof.

Preferred embodiments of the formula(Ia) include:
The compound of the formula(Ia) as described in the broadest embodiment above and wherein:
$R_1$ is $C_{1-8}$ alkyl or branched alkyl, $C_{3-8}$ alkenyl or branched alkenyl, $C_{3-8}$ alkynyl or branched alkynyl, $C_{3-8}$ cycloalkyl, $C_{1-3}$ alkyloxy$C_{1-3}$ alkyl, $C_{1-5}$ alkyloxy, $C_{1-3}$ alkylthio$C_{1-3}$ alkyl, $C_{1-5}$ alkylthio, $CF_3$, heterocyclyl selected from tetrahydrofuranyl, pyridyl, furanyl or thiazolyl or aryl optionally substituted with halogen, $C_{1-4}$ alkyl, CN, alkyloxy or $(CH_3)_2N$;
$R_2$ is H;
$R_3$ is halogen, methyl, ethyl, $CF_3$, CN, cyclopropyl, vinyl, $SCH_3$, methoxy, heterocyclyl selected from tetrahydrofuranyl, pyridyl, furanyl or thiazolyl or aryl optionally substituted with halogen, $C_{1-4}$ alkyl, CN, methoxy or $(CH_3)_2N$;
L is —NHC(O)—, —NH—, —NHCH$_2$—, —NHC(O)NH, and
$R_4$ is $C_{1-6}$ alkyl, carbocyclyl or heterocyclyl selected from pyridyl, pyrimidinyl, pyrazinyl, pyridazinyl, morpholinyl, thiomorpholinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl, each optionally substituted with one or more halogen, —CN, alkylthio, alkylsulfinyl, alkylsulfonyl, —NO$_2$, SO$_2$NH$_2$ or $R_7$ where $R_7$ is $C_{1-6}$ alkyl, $C_{2-6}$ alkenyl, $C_{1-6}$ alkyloxyalkyl, $C_{1-4}$ alkyloxy, $C_{1-5}$ alkylamino, or $C_{1-6}$ alkylthioalkyl each optionally substituted with OH, CN, —COO-lower alkyl, —CONH-lower alkyl, —CON (lower alkyl)$_2$, dialkylamino, phenyl or heterocyclyl as hereinabove described in this paragraph; and
$R_8$ is NH$_2$.

In another embodiment, there is provided compounds of the formula(Ia) as described in the embodiment immediately above and wherein:
$R_1$ is ethyl, isopropyl, n-propyl, t-butyl, cyclopentyl, $CF_3$, ethoxy, $CH_3OCH_2$-, 2- or 3-tetrahydrofuranyl, 2-, 3-, or 4-pyridyl, 2-furanyl, or 2-thiazolyl;
$R_3$ is CN, $CF_3$, Cl, methyl, ethyl, $SCH_3$, cyclopropyl, vinyl or 2-furanyl;
L is —NHC(O)—, and
$R_4$ is a phenyl or pyridyl each optionally substituted with one to three halogen, —CN, alkylthio, alkylsulfmyl, alkylsulfonyl or $R_7$ where $R_7$ is $C_{1-6}$ alkyl, $C_{2-6}$ alkenyl, $C_{1-6}$ alkyloxy$C_{1-6}$ alkyl, $C_{1-4}$ alkyloxy, $C_{1-5}$ alkylamino each optionally substituted with halogen, OH, CN, COO-lower alkyl, —CONH-lower alkyl, —CON(lower alkyl)$_2$, dialkylamino, phenyl, morpholinyl or pyridyl.

In yet another embodiment, there is provided compounds of the formula(Ia) as described in the embodiment immediately above and wherein:
$R_1$ is isopropyl, $CF_3$, 3-pyridyl or 4-pyridyl;
$R_2$ is H;

$R_3$ is CN, $CF_3$, Cl, methyl, $SCH_3$ or ethyl; and
$R_4$ is a phenyl or pyridyl each optionally substituted with one to three groups selected from halogen, —CN, alkylthio, alkylsulfinyl, alkylsulfonyl or $R_7$ where $R_7$ is $C_{1-6}$ alkyl, $C_{1-4}$ alkyloxy, $C_{1-5}$ alkylamino each optionally substituted with OH, CN, COO-lower alkyl, —CONH-lower alkyl, —CON(lower alkyl)$_2$, dialkylamino, phenyl, morpholinyl or pyridyl.

A particularly preferred embodiment of formula Ia is

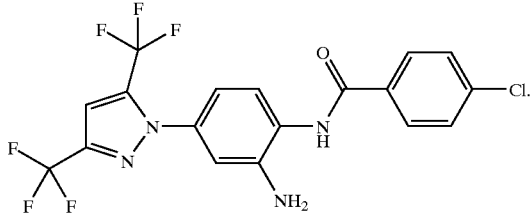

Any of the of compounds of formulas I or Ia containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formulas I or Ia can exist in more than one tautomeric form. The invention includes use of all such tautomers.

The compounds of formulas I or Ia are only those which are contemplated to be 'chemically stable' as will be appreciated by those skilled in the art. For example, compounds which would have a 'dangling valency', or a 'carbanion' are not compounds contemplated to be used in the methods of the invention.

All terms as used herein in this specification, unless otherwise stated, shall be understood in their ordinary meaning as known in the art. All alkyl, alkylene, alkenyl, alkenylene, alkynyl and alkynylene groups shall be understood as being $C_{1-10}$, branched or unbranched unless otherwise specified. Other more specific definitions are as follows:

A "pharmaceutically acceptable derivative" refers to any pharmaceutically acceptable salt or ester of a compound of this invention, or any other compound which, upon administration to a patient, is capable of providing (directly or indirectly) a compound used in this invention, a pharmacologically active metabolite or pharmacologically active residue thereof.

The term "metabolite" shall be understood to mean any of the compounds of the formula I or Ia which are capable of being hydroxylated or oxidized, enzymatically or chemically, as will be appreciated by those skilled in the art.

The term "acyl", when used alone or in combination with another group, shall be understood to mean an R—(C=O)— moiety wherein R is an alkyl group. Examples of R can be a $C_{1-10}$ alkyl, saturated or unsaturated, branched or unbranched. The term "acyloxy" shall be understood to mean an R—CO$_2$— group wherein R is as defined in this paragraph. Likewise, "acylthio" shall be understood to mean an R—C(O)—S— group wherein R is as defined in this paragraph. "Alkyloxy" shall be understood to mean an R—O— group wherein R is as defined in this paragraph The term "alkylene" shall be understood to mean a saturated, divalent $C_{1-10}$ hydrocarbon chain, i.e., generally present as a bridging group between two other groups. Examples of alkylene groups include —CH$_2$— (methylene); —CH$_2$CH$_2$— (ethylene); —CH$_2$CH$_2$CH$_2$— (propylene) etc.

The term "alkenylene" shall be understood to mean a divalent $C_{1-10}$ hydrocarbon chain having one or more double bonds within the chain, i.e., generally present as a bridging group between two other groups. Examples of alkenylene groups include —CH=CH— (ethenylene); —CH=CHCH$_2$— (1-propenylene), —CH=CHCH$_2$CH$_2$— (1-butenylene), —CH$_2$CH=CHCH$_2$— (2-butenylene), etc.

The term "alkynylene" shall be understood to mean a divalent $C_{1-10}$ hydrocarbon chain having one or more triple bonds within the chain, i.e., generally present as a bridging group between two other groups. Examples of alkenylene groups include —C≡C—; —C≡CCH$_2$—; —C≡CCH$_2$CH$_2$—; —CH$_2$C≡CCH$_2$—, etc.

The term "aryl" shall be understood to mean a 6–10 membered aromatic carbocycle; "aryl" includes, for example, phenyl and naphthyl; other terms comprising "aryl" will have the same definition for the aryl component, examples of these moieties include: arylalkyl, aryloxy or arylthio.

The term "cycloalkenyl" shall be understood to mean a $C_{3-10}$ cycloalkyl group wherein one or more of the single bonds in the cycloalkyl ring are replaced by double bonds.

The terms "cycloalkylene" and "cycloalkenylene" shall be understood to mean divalent $C_{4-10}$ cycloalkyl and $C_{4-10}$ cycloalkenyl groups, respectively, i.e., generally present as bridging groups between two other groups.

The term "halogen" as used in the present specification shall be understood to mean bromine, chlorine, fluorine or iodine.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Example "heteroaryl" radicals include, pyridyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl,or a fused heteroaryl such as cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene;

The term "heterocycle" refers to a stable 5–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached to the main structure by any atom of the cycle, which results in the creation of a stable structure. Example "heterocycle" radicals include pyrrolinyl, pyrrolidinyl, pyrazolinyl, pyrazolidinyl, 1,2,5,6-tetrahydropyridinyl, piperidinyl, morpholinyl, thiomorpholinyl, pyranyl, thiopyranyl, piperazinyl, indolinyl, and 1,2,3,3a,4,6a-hexahydro-cyclopenta[c]pyrrolyl.

As used herein and throughout this specification, the terms "nitrogen" and "sulfur" and their respective elements symbols include any oxidized form of nitrogen and sulfur and the quaternized form of any basic nitrogen.

The "$C_{6-12}$ bridged carbocyclic ring system, optionally having one to three double bonds in the ring system" shall be understood to mean any carbocyclic ring system containing 6 to 12 carbon atoms and having at least one bridged-type fusion within the ring system. An example is a $C_{6-10}$carbocyclic ring system, optionally having one or two double bonds in the system. Examples of such a ring system are bicyclo[2.2.1]heptane and adamantane.

Methods of making all compounds described herein are those methods well known in the art and in particular those described in WO 99/62885, and the cited methods therein, are incorporated herein by reference in their entirety.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

Methods fo Use

In accordance with the invention, there are provided methods of using the compounds of the formulas I or Ia. The compounds used in the invention prevent the degradation of sEH substrates that have beneficial effects or prevent the formation of metabolites that have adverse effects. The inhibition of sEH is an attractive means for preventing and treating a variety of cardiovascular diseases or conditions e.g., endothelial dysfunction. Thus, the methods of the invention are useful for the treatment of such conditions. These encompass diseases including, but not limited to, type 1 and type 2 diabetes, insulin resistance syndrome, hypertension, atherosclerosis, coronary artery disease, angina, ischemia, ischemic stroke, Raynaud's disease and renal disease.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds described herein may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the above-described compounds include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

EXAMPLES

Example I

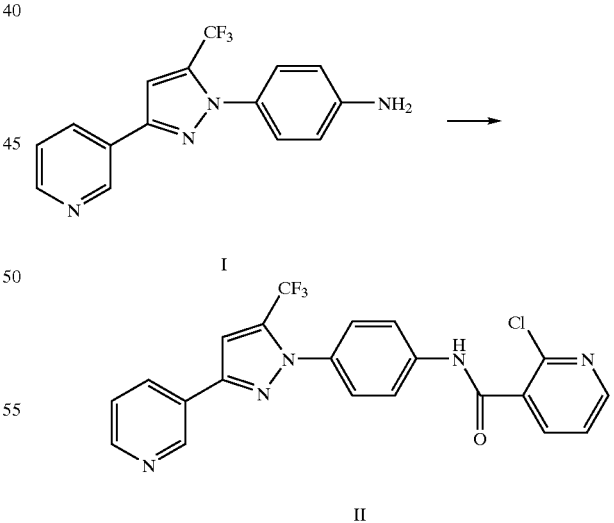

To a solution of 2-chloroniotinic acid (0.78 g) in acetonitrile (25 mL) cooled on ice was added EDC (1.1 g). After 10 minutes, the aniline I (1.0 g) was added. The mixture was stirred on ice for 1 hour and then allowed to warm to room temperature. The solid product II was collected by filtration (1.2 g).

II →

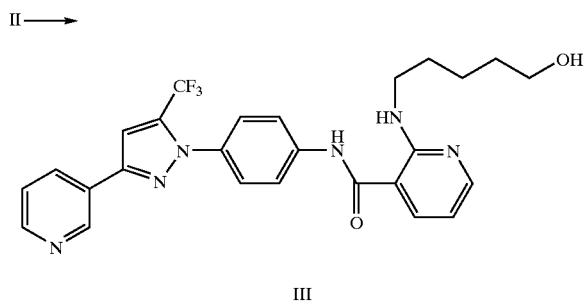

III

A mixture of II (0.1 g) and 5-amino pentanol (0.047 g) in dioxane (2 mL) was heated at 120° C. in a sealed tube, overnight. The mixture was cooled, diluted with ethyl acetate, washed with water, dried, filtered and evaporated. Purification by preparative layer chromatography gave III as a solid (0.05 g), mp 95–96° C.

II →

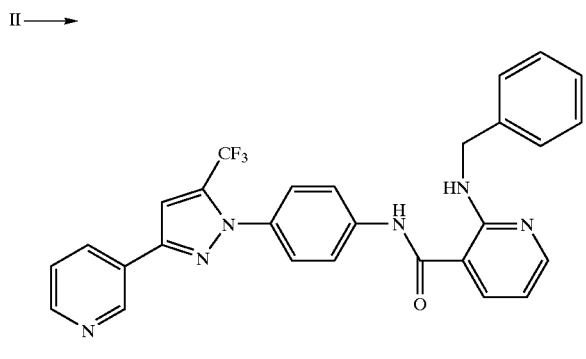

IV

A mixture of II (0.1 g) and benzylamine (1.5 mL) was heated in a sealed tube at 120° C. overnight. The mixture was cooled, diluted with methylene chloride, washed with water, dried filtered and evaporated. Chromatography of the residue over silica gel gave IV (0.06 g), mp 183–184° C.

II →

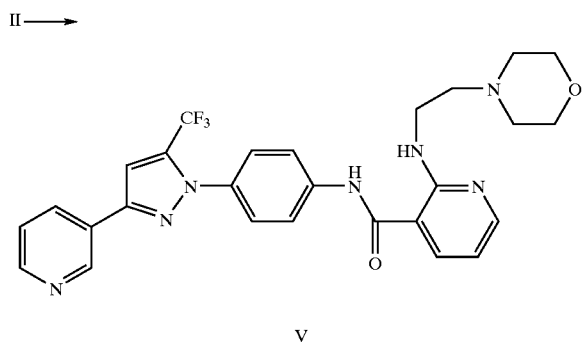

V

A mixture of II (0.1 g) and aminoethylmorpholine (0.059 g) in dioxane (2 mL) was heated at 120° C. in a sealed tube, overnight. The mixture was diluted with ethyl acetate, washed with water, dried, filtered and evaporated. Chromatography of the residue over silica gel gave V (0.045 g) mp 85–87° C.

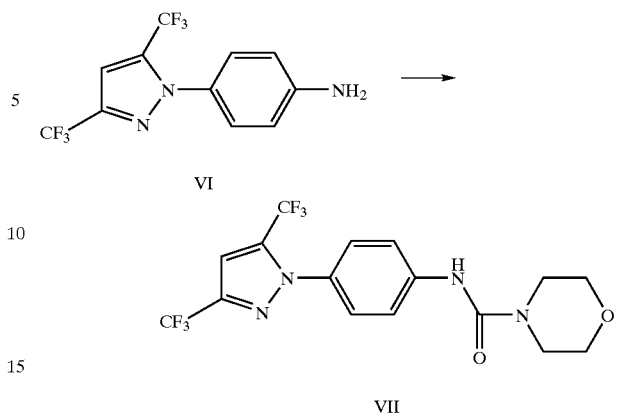

VI

VII

To a solution of VI (0.3 g) in methylene chloride (5 mL) was added diisopropylethylamine (0.18 mL) followed by 4-morpholine carbonyl chloride (0.11 mL). The mixture was stirred at room temperature for 3 days. The mixture was diluted with ethyl acetate, washed with water, dried, filtered and evaporated. Chromatography of the residue over silica gel gave VII (0.8 g) mp 185–186° C.

I →

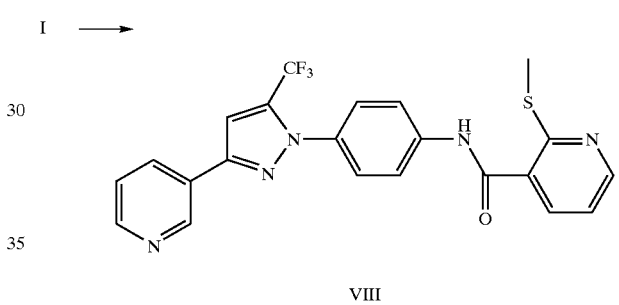

VIII

To a solution of 2-thiomethyl nicotinic acid (0.217 g) in acetonitrile cooled on ice, was added EDC (0.27 g). After 10 minutes, I (0.30 g) was added along with DMAP (catalytic amount). The mixture was stirred on ice for 1 hour and then allowed to stir at room temperature overnight. The mixture was diluted with ethyl acetate, washed with water, dried filtered and evaporated to give (VIII).

VIII →

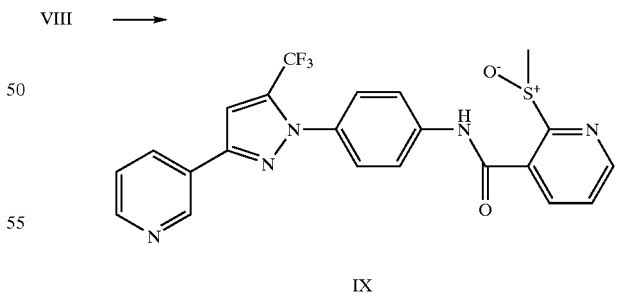

IX

To a solution of VIII (0.09 g) in methylene chloride (7 mL) cooled on ice, was added m-chloroperbenzoic acid (0.043 g). After 10 minutes, the reaction mixture was washed with aqueous sodium bicarbonate, dried, filtered and evaporated. Purification by preparative layer chromatography gave (IX) (0.017 g), mp 243–244° C.

Compounds with $R_8$=$NH_2$ or mono-or-dialkylamino, may be prepared by the methods described below.

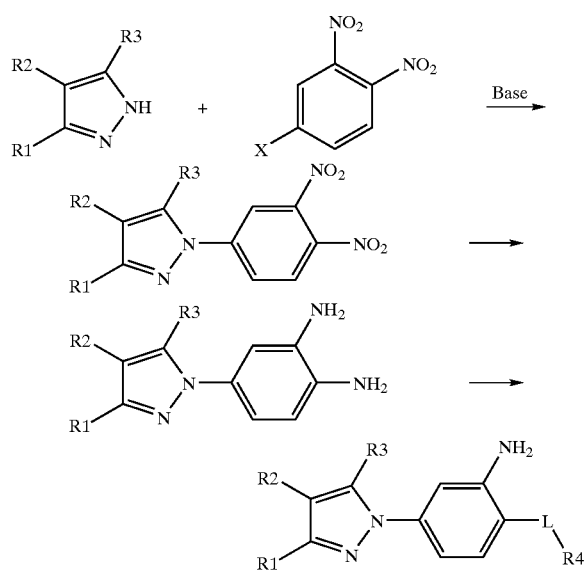

A 3,5-disubstituted pyrazole may be reacted with dinitrobenzene substituted in the 4-position with a leaving group such as a halogen in the presence of a base. The nitrophenylpyrazoles produced by either method could then be reduced to diaminophenyl pyrazoles by using a reducing agent such as SnCl$_2$ or hydrogen or a hydrogen source such as ammonium formate in the presence of a catalyst such as palladium. The diamino compound could then be converted to compounds of Formula 1 (R$_8$=NH$_2$, or mono-or-dialkylamino) by methods previously described.

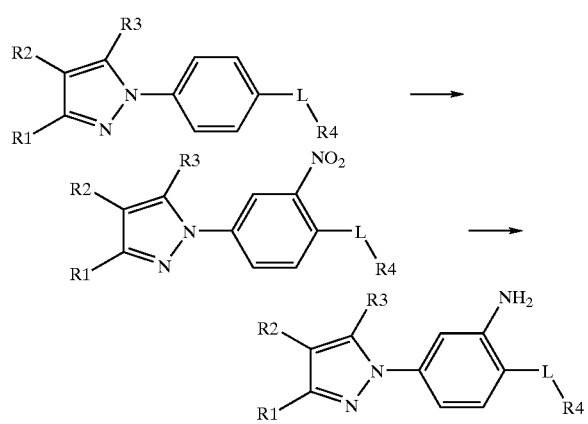

Alternatively, a compound of Formula I (where R$_8$=H) can be reacted with a nitrating reagent such as nitronium tetrafluoroborate to provide the nitrated intermediate shown above. Reduction of the nitro group by using a reducing agent such as SnCl$_2$ or hydrogen or a hydrogen source such as ammonium formate in the presence of a catalyst such as palladium then provides the compounds of formula I/Ia where R$_8$=NH$_2$. Alkylation of the NH$_2$ by methods known in the art provides compounds with R$_8$=mono, dialkylamine. For example treatment with formaldehyde and formic acid results in R$_8$=NMe$_2$.

Example II

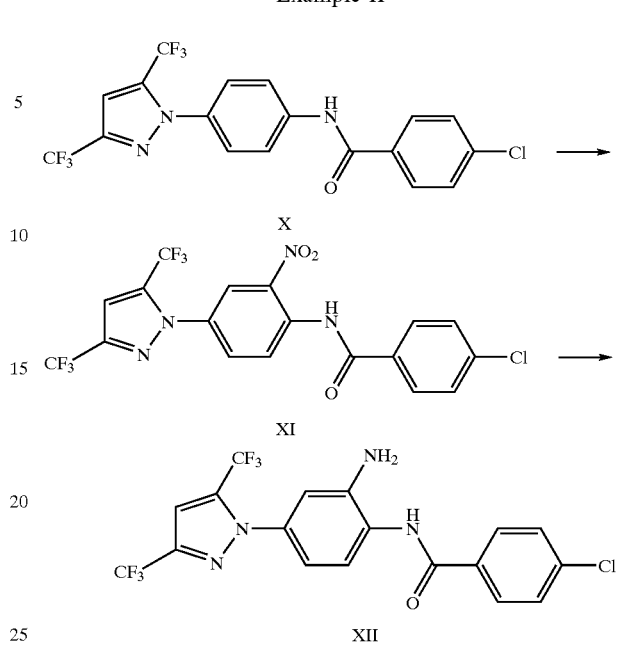

To a solution of X (0.65 g) in acetonitrile (10 mL) and methylene chloride (3 mL) cooled on ice was added nitronium tetrafluoroborate (0.575 g) in two portions over 10 minutes. After 10 minutes, the reaction was quenched by addition of saturated aqueous sodium bicarbonate. Ethyl acetate was added and the organic phase was washed with water, dried, filtered and evaporated. Crystallization of the product from ethanol/methylene chloride gave XI (0.597 g).

To a solution of XI (0.22 g) in acetic acid (10 mL) was added a solution of stannous chloride (0.73 g) in conc. HCl (5 mL). Additional acetic acid (5 mL) was added and the mixture was stirred at room temperature for 6 hours. The mixture was neutralized with aqueous KOH and extracted with methylene chloride. The organic phase was dried, filtered and evaporated to give XII (0.18 g), mp 201–203° C.

Preferred embodiments of the invention include methods of using particular inhibitors which have been found to be surprisingly effective at inhibiting the sEH enzyme. Methods employed for selecting such inhibitors include the fluorescence polarization assay summarized below and are described in U.S. provisional application Ser. No. 60/282,575, incorporated herein by reference in it's entirety.

Fluorescence Polarization Assay to Determine Inhibition of sEH:

Step One: Characterization of the Fluorescent Probe

The wavelengths for maximum excitation and emission of the fluorescent probe should first be measured. An example of such a probe is compound (4) as shown in U.S. Ser. No. 60/282,575, where these values are 529 nm and 565 nm, respectively. These fluorescence wavelength values were measured on an SLM-8100 fluorimeter with the probe dissolved in an assay buffer (20 mM TES, pH 7.0, 200 mM NaCl, 0.05% (w/v) CHAPS, 2 mM DTT).

The affinity of the probe for sEH was then determined in a titration experiment. The fluorescence polarization value of compound 4 in assay buffer was measured on an SLM-8100 fluorimeter using the excitation and emission maximum values described above. Aliquots of sEH were added and fluorescence polarization was measured after each addition until no further change in polarization value was observed. Non-linear least squares regression analysis was used to calculate the dissociation constant of compound 4 from the polarization values obtained for sEH binding to compound 4. FIG. 1 shows the results from this titration experiment Step Two: Screening for Inhibitors of Probe Binding In order to screen a large number of compounds the assay was performed using a 96-well plate format. An example of such a plate is the Dynex Microfluor 1, low protein binding U-bottom black 96 well plates (#7005). The plate is set up by first creating a complex between recombinant human sEH and a fluorescent probe that binds to the active site of sEH. In this example, the complex between compound 4 and sEH, was pre-formed in assay buffer (20 mM TES, pH 7.0, 200 mM NaCl, 0.05% (w/v) CHAPS, 1 mM TCEP). The concentrations of sEH and compound 4 in this solution were made up such that the final concentration in the assay was 10 nM sEH and 2.5 nM compound 4. Test compounds were then serially diluted into assay buffer, across a 96 well plate The pre-formed sEH-probe complex was then added to all the wells and incubated for 15 minutes at room temperature. The fluorescence polarization was then measured using a fluorescence polarization plate reader set at the wavelengths appropriate for the fluorescent label on the fluorescent probe (4). In this example, an LJL Analyst was set to read rhodamine fluorescence polarization (Ex 530 nM, Em 580 nM). Non-linear least squares regression analysis was then used to calculate dissociation constants for the test compounds binding to sEH from the polarization values for the probe binding to sEH in the presence of the test compounds.

Results which show a decrease in fluorescence polarization of the probe-sEH complex in the presence of the test compound is evidence that this test compound is a competitive inhibitor of soluble epoxide hydrolase that competes with the fluorescent probe for sEH active site binding.

What is claimed is:

1. A method of treating a condition caused by endothelial dysfunction, chosen from insulin resistance syndrome, hypertension, angina, ischemia, ischemic stroke, renal disease and Raynaud's disease, said method comprising administering to a patient in need thereof a therapeutically effective amount of a compound of Formula I:

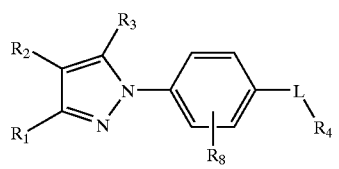

(I)

wherein:
$R_1$ and $R_3$ are the same or different and each is $CF_3$, halogen, CN, $C_{1-8}$ alkyl or branched alkyl, $C_{2-8}$ alkenyl or $C_{3-8}$ branched alkenyl, $C_{2-8}$ alkynyl or $C_{3-8}$ branched alkynyl, $C_{3-8}$ cycloalkyl optionally substituted with OH, CN or methoxy, $C_{1-8}$ alkyloxy, $C_{1-4}$ alkyloxy$C_{1-4}$ alkyl, $C_{1-8}$ alkylthio, $C_{1-4}$ alkylthio$C_{1-4}$alkyl, $C_{1-8}$ dialkylamino, $C_{1-4}$ dialkylaminoalkyl, $CO_2R_5$ where $R_5$ is $C_{1-4}$ alkyl or $C_{2-4}$ alkenyl optionally substituted with carbocyclyl or heterocyclyl, aryl or $R_1$, is heterocyclyl connected to the pyrazole in any position that makes a stable bond optionally substituted with halogen, $C_{1-4}$ alkyl, $C_{2-4}$ alkenyl, CN, $(CH_3)_2N$, $CO_2CH_3$, alkyloxy, aryl, heterocyclyl or $R_5$;

$R_2$ is H, halogen or methyl;

L is —NHC(O)—, —NHC(O)O— or —NHC(O)C(O)—, $R_4$ is $C_{1-8}$ alkyl, $C_{1-8}$ alkyloxy, $C_{1-8}$ alkylthio, $C_{1-8}$ alkylamino, $C_{1-4}$ alkyloxyalkyl, $C_{1-4}$ alkylthioalkyl, $C_{1-4}$alkylaminoalkyl, $C_{1-4}$dialkylaminoalkyl, carbocyclyl or heterocyclyl each optionally substituted with one or more halogen, —CN, —$NO_2$, $SO_2NH_2$ alkylthio, alkylsulfinyl, alkylsulfonyl or $R_7$ where $R_7$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-4}$ alkyloxy, $C_{1-5}$ alkylamino, $C_{1-6}$ alkylthioalkyl, $C_{1-6}$ alkylsulfmylalkyl or $C_{1-6}$ alkylsulfonylalkyl, each $R_7$ in turn is optionally substituted with halogen, OH, alkyloxy, CN, COO-lower alkyl, —CONH-lower alkyl, —CON(lower alkyl)$_2$, dialkylamino, phenyl or heterocylcyl;

$R_8$ is H;

or the pharmaceutically acceptable salts thereof;

with the proviso that when $R_3$ is alkyl or $CF_3$ and $R_4$ is pyridyl, then the pyridyl is substituted except that the substituents on the pyridyl cannot be halogen; and with the proviso that the following compounds are excluded: N-[4-(5-ethyl-3-pyridin-3-yl-pyrazol-1-yl)-phenly] nicotinamide; N-[4-(5-Ethyl-3-pyridin-3-yl-pyrazol-1yl)phenyl]-1-methylindole-2-carboxamide; 4-(3-Cyanopropoxy)-N-[4-(5-cyano-3-pyridin-3-yl-pyrazol-1-yl)phenyl]benzamide; and N-[4-(5-cyano-3-pyridin-3-yl-pyrazol-1yl)phenyl]-4-(3-[1,3]dioxolan-2-yl-propoxy)benzamide.

2. The method according to claim 1 and wherein:

in formula (I):

$R_1$ is $C_{1-8}$ alkyl or branched alkyl, $C_{3-8}$ alkenyl or branched alkenyl, $C_{3-8}$ alkynyl or branched alkynyl, $C_{3-8}$ cycloalkyl, $C_{1-3}$ alkyloxy$C_{1-3}$ alkyl, $C_{1-5}$ alkyloxy, $C_{1-3}$ alkylthio$C_{1-3}$ alkyl, $C_{1-5}$ alkylthio, $CF_3$, heterocyclyl selected from tetrahydrofuranyl, pyridyl, furanyl or thiazolyl or aryl optionally substituted with halogen, $C_{1-4}$ alkyl, CN, alkyloxy or $(CH_3)_2N$;

$R_2$ is H;

$R_3$ is halogen, methyl, ethyl, $CF_3$, CN, cyclopropyl, vinyl, $SCH_3$, methoxy, or aryl optionally substituted with halogen, $C_{1-4}$ alkyl, CN, methoxy or $(CH_3)_2N$;

L is —NHC(O)—, $R_4$ is $C_{1-6}$ alkyl, carbocyclyl or heterocyclyl selected from pyridyl, pyrimidinyl, pyrazinyl, pyridazinyl, morpholinyl, thiomorpholinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl, each optionally substituted with one or more halogen, —CN, alkylthio, alkylsulfinyl, alkylsulfonyl , —$NO_2$, $SO_2NH_2$ or $R_7$ where $R_7$ is $C_{1-6}$ alkyl, $C_{2-6}$ alkenyl, $C_{1-6}$ alkyloxyalkyl, $C_{1-4}$ alkyloxy, $C_{1-5}$ alkylamino, or $C_{1-6}$ alkylthioalkyl each optionally substituted with OH, CN, —COO-lower alkyl, —CONH-lower alkyl, —CON(lower alkyl)$_2$, dialkylamino, phenyl or heterocyclyl as hereinabove described in this paragraph.

3. The method according to claim 2 and wherein:

in the formula (I)

$R_1$ is ethyl, isopropyl, n-propyl, t-butyl, cyclopentyl, $CF_3$, ethoxy, $CH_3OCH_2$—, 2- or 3-tetrahydrofuranyl, 2-, 3-, or 4-pyridyl, 2-furanyl, or 2-thiazolyl;

$R_3$ is CN, $CF_3$, Cl, methyl, ethyl, $SCH_3$, cyclopropyl, or vinyl; and $R_4$ is a phenyl or pyridyl each optionally substituted with one to three halogen, —CN, alkylthio, alkylsulfinyl, alkylsulfonyl or $R_7$ where $R_7$ is $C_{1-6}$ alkyl, $C_{2-6}$ alkenyl, $C_{1-6}$ alkyloxy$C_{1-6}$ alkyl, $C_{1-4}$ alkyloxy, $C_{1-5}$ alkylamino each optionally substituted with halogen, OH, CN, COO-lower alkyl, —CONH-lower alkyl, —CON(lower alkyl)$_2$, dialkylamino, phenyl, morpholinyl or pyridyl.

4. The method according to claim 3 and wherein:

in the formula (I)

$R_1$ is isopropyl, $CF_3$, 3-pyridyl or 4-pyridyl;

$R_2$ is H;

$R_3$ is CN, $CF_3$, Cl, methyl, $SCH_3$ or ethyl; and $R_4$ is a phenyl or pyridyl each optionally substituted with one to three groups selected from halogen, —CN, alkylthio, alkylsulfinyl, alkylsulfonyl or $R_7$ where $R_7$ is $C_{1-6}$ alkyl, $C_{1-4}$ alkyloxy, $C_{1-5}$ alkylamino each optionally substituted with OH, CN, COO-lower alkyl, —CONH-lower alkyl, —CON(lower alkyl)$_2$, dialkylamino, phenyl, morpholinyl or pyridyl.

5. The method according to claim 1 wherein the condition is hypertension.

6. The method according to claim 1 wherein the compound is chosen from:

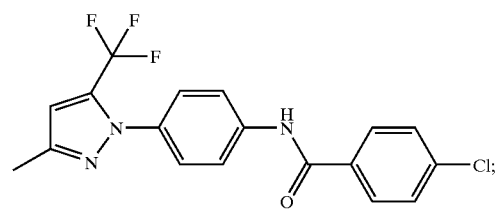

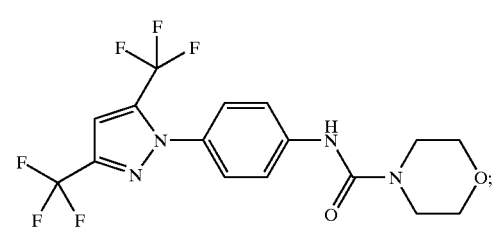

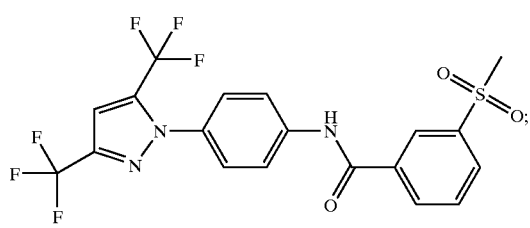

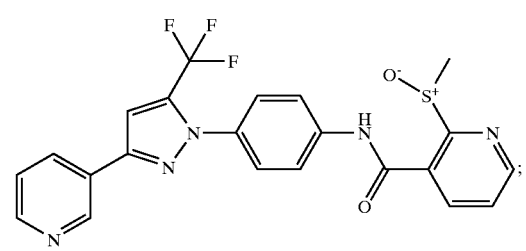

-continued

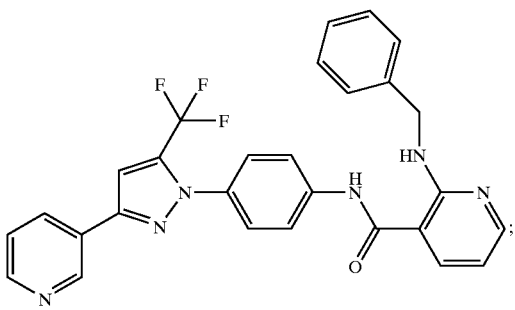

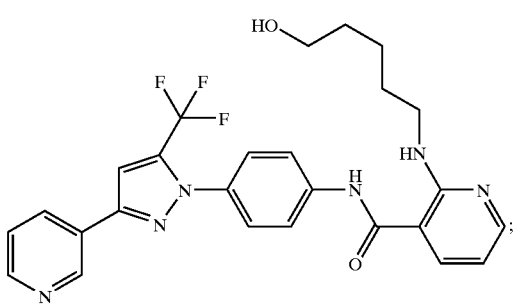

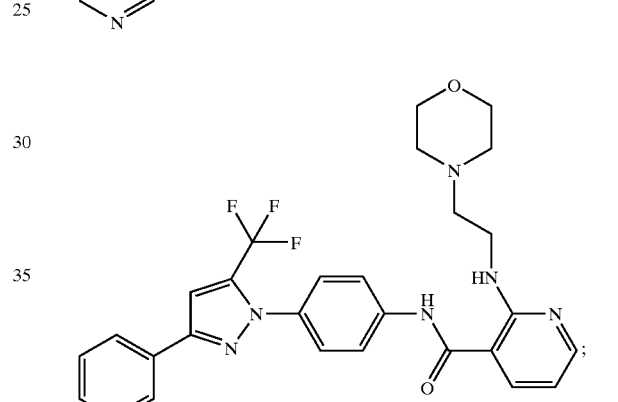

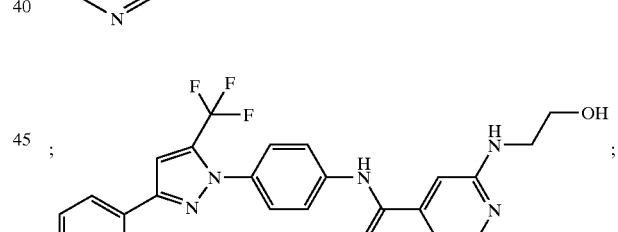

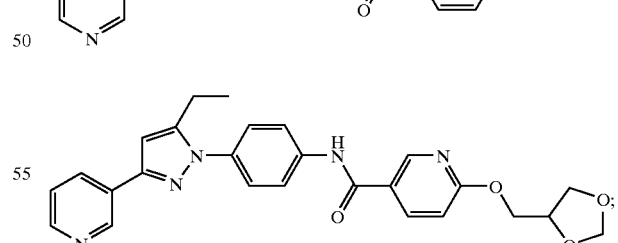

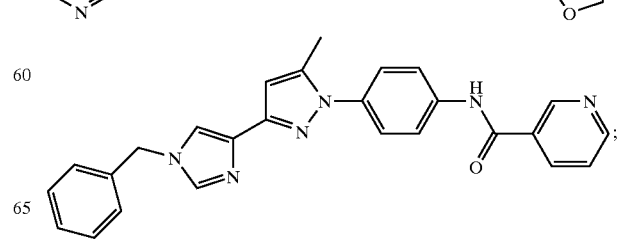

-continued
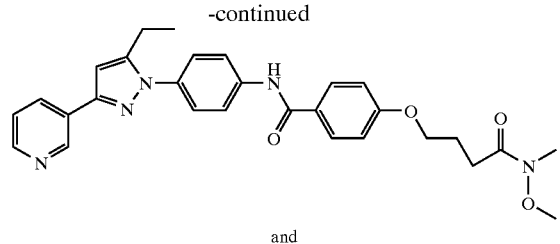
and
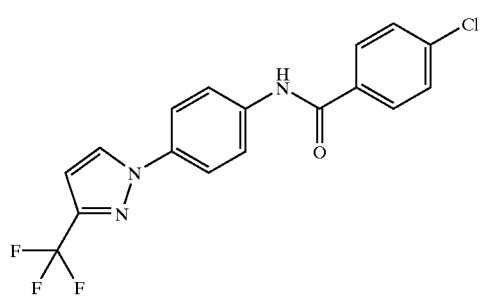
or the pharmaceutically acceptable salts thereof.
7. The method according to claim 1 or 5 wherein the compound is chosen from:
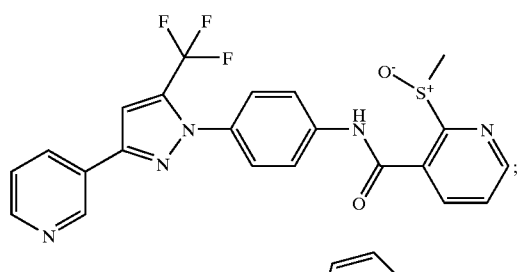
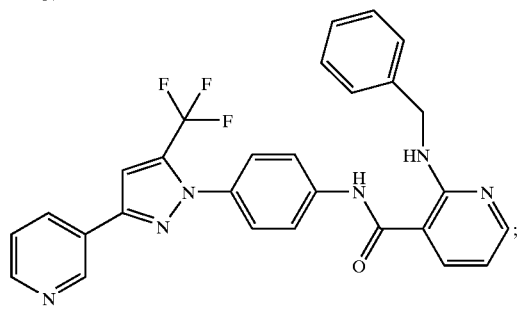
-continued
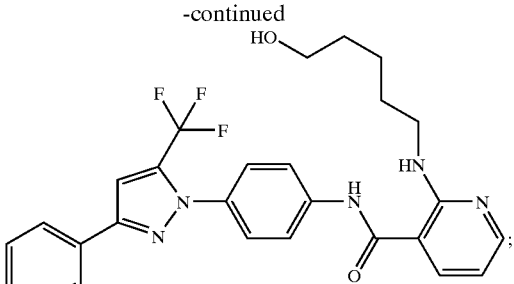
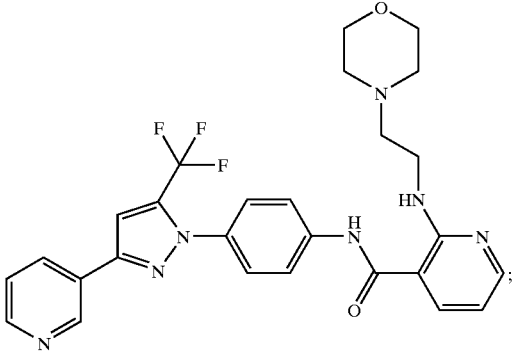
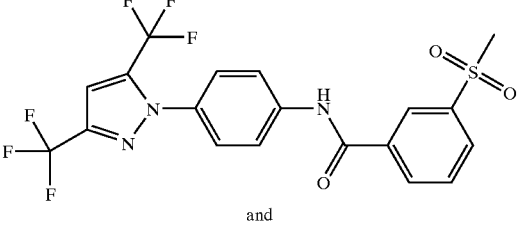
and
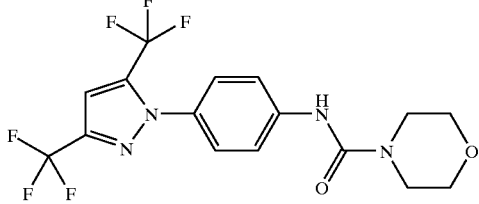
or the pharmaceutically acceptable salts thereof.
* * * * *